| United States Patent [19] | [11] 3,962,330 |
| --- | --- |
| Cotti | [45] June 8, 1976 |

[54] PROCESS FOR THE PREPARATION OF 6-DEMETHYL-6-DEOXY-6-METHYLENE-TETRACYCLINES

[75] Inventor: Gino Cotti, Monza (Milan), Italy

[73] Assignee: Ankerfarm, S.p.A., Milan, Italy

[22] Filed: Sept. 24, 1974

[21] Appl. No.: 509,054

[30] Foreign Application Priority Data
Sept. 28, 1973  Italy.................................. 29488/73

[52] U.S. Cl. .......................................... 260/559 AT
[51] Int. Cl.² ........................................ C07C 103/22
[58] Field of Search.............................. 260/559 AT

[56] References Cited
UNITED STATES PATENTS

| 3,250,809 | 5/1966 | Blackwood et al........... 260/559 AT |
| 3,649,700 | 3/1972 | Baader et al.................... 260/654 D |
| 3,659,006 | 4/1972 | Pande............................. 260/465.7 |

OTHER PUBLICATIONS
Borowitz et al., JACS, 94:19, Sept. 20, 1972, pp. 6817–6822.

*Primary Examiner*—C. Davis
*Attorney, Agent, or Firm*—Stevens, Davis, Miller & Mosher

[57] ABSTRACT

The invention relates to the preparation of 6-demethyl-6-deoxy-6-methylene-tetracycline by means of reductive dehalogenation of the corresponding 11a-halo-6-demethyl-6-deoxy-6-methylene-tetracycline, the reaction being carried out in presence of the stoichiometric quantity of a tertiary phosphine, arsine or stibine and in a polar solvent. The time and temperature of the reaction are controlled within specified limits to obtain a complete conversion.

4 Claims, No Drawings

PROCESS FOR THE PREPARATION OF 6-DEMETHYL-6-DEOXY-6-METHYLENE-TETRACYCLINES

The present invention relates to a process for the preparation of 6-demethyl-6-deoxy-6-methylene-tetracyclines by means of dehalogenation of the corresponding 11a-halo-6-demethyl-6-deoxy-6-methylene tetracyclines.

More exactly, the process according to the invention consists of a reductive dehalogenation, effected with the use of a tertiary phosphine or arsine or stibine, in an inert solvent in the conditions of reaction.

Starting from compounds of the type:

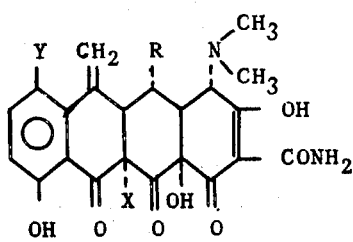

in which
X = halogen
R = H, OH, —O—CO—R'' (R' = alkyl group containing from 1 to 6 C atoms)
Y = H, halogen
or starting from their mineral or organic acid salts, or from their complexes with the salts of the polyvalent metals, there are obtained the corresponding 6-methylene-tetracyclines of the type:

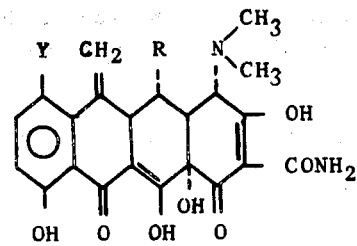

in which Y, R have the aforesaid meaning.

The compounds having the formula II are known antibiotics, endowed with notable activity against many pathogenic organisms and in the British Pat. Nos. 951,663, 955,031, the U.S. Pat. No. 2,984,686, German Pat. No. 2,037,292 description is given of their preparation with the use of reducing agents such as sodium hydrosulfite, zinc powder in acid environment and hydrogen in the presence of noble metal catalysts. The present invention is based on the use in appropriate conditions of tertiary phosphines, arsines or stibines to bring about the reductive elimination of the atom of halogen at 11A.

Particularly indicated is triphenylphosphine, which reacts according to the scheme;

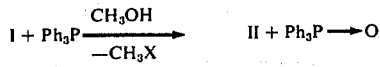

in which
X = halogen.

According to the process of the present invention a compound of the group of the tetracyclines having general formula I and a stoichiometric quantity of tertiary phosphine, arsine or stibine are placed into contact in an appropriate solvent at suitable temperature and concentrations for the period of time sufficient to obtain the complete conversion into the corresponding compound having the formula II.

Conventional methods are employed to separate the 6-demethyl-6-deoxy-6-methylene-tetracyclines from the reaction solution.

Suitable solvents are the mono or polyhydroxylated alcohols having from 1 to 4 carbon atoms, methoxyethanol, ethoxyethanol and their mixtures with dioxane, tetrahydrofurane, acetonitrile, N,N'-dimethyl-formamide, acetone.

The speed of reaction and the extent of the conversion depend on the temperature: at temperatures lower than 20°C the reaction is excessively slow while temperatures higher than 80°C can cause the decomposition of the starting substance. The preferred temperature are comprised between 20°C and 80°C.

The reaction time necessary for a complete conversion depends on the temperature, but is generally within 30–60 minutes.

The reaction is conducted in inert gas atmosphere in order to exclude the presence of oxygen which could convert the triphenylphosphine into inactive triphenylphosphine-oxide.

The optimal quantity of triphenylphosphine is 1 mole per mole of tetracycline; smaller amounts lead to incomplete conversions and larger amounts give no advantage.

The 6-demethyl-6-deoxy-6-methylene tetracyclines obtained can be crystallized as hydrochloride of excellent analytical properties directly from the crude reaction solution.

There are now given some non-restrictive Examples of the execution of the present invention.

EXAMPLE I 40.5 g of $Ph_3P$ was added to 100 g of 11a-chloro-6-demethyl-6-deoxy-6-methylene-5-oxytetracycline p-toluenesulfonate in 950 ml of MeOH.

The solution was heated to 60°C, kept under agitation for 30 minutes and then concentrated at low pressure to 250 ml.

Addition was made of 250 ml of $Me_2CO$ and 100 ml of 37% HCl.

The resultant solution was maintained for 30 minutes at 60°C under agitation; after slow cooling to 10°–15°C filtration was performed and the precipitate obtained was washed with acetone and vacuum dried at 40°C; there was obtained 61.5 g of 6-demethyl-6-deoxy-6-methylene-5-oxytetracycline giving a spectrophotometric assay value of 98%.

EXAMPLE II

To 20.8 g of 11a-chloro-6-demethyl-6-deoxy-6-methylene-5-oxytetracycline hydrofluoride in a mixture of 50 ml of MeOH and 50 ml of $Me_2CO$, addition made of 11 g of $Ph_3P$ and heating to 60°C was effected.

After 30 minutes cooling was effected to 20°C and addition made of 30 ml of 37% HCl, heating to 50°C was effected and, after 60 minutes, slow cooling was effected to 15°–20°C; filtration was then performed, and washing with acetone.

The product obtained, vacuum dried at 50°C, weighed 16.1 g and gave a spectrophotometric assay value of 98.5%.

EXAMPLE III

To 8 g of 11a-bromo-6-demethyl-6-deoxy-6-methylene-5-oxytetracycline, anhydrous, dissolved in 80 ml of THF and 20 ml of MeOH, addition was made of 4 g of $Ph_3P$ and the whole was kept at 40°C for 2 hours.

At the end of that period there was found to have taken place an almost complete conversion into 6-demethyl-6-deoxy-6-methylene-5-oxytetracycline.

EXAMPLE IV 4.88 g of 11a-fluoro-6-demethyl-6-deoxy-6-methylene-5-oxytetracycline hydrofluoride was treated in the manner described in Example II. There were obtained 4.1 g of 6-demethyl-6-deoxy-6-methylene-5-oxytetracycline hydrochloride giving a spectrophotometric assay value of 97.5%.

EXAMPLE V 69.2 g of 11a-chloro-6-demethyl-6-deoxy-6-methylene-5-acetoxytetracycline mesylate was treated with 26.2 g of $Ph_3P$ in boiling MeOH.

Complete conversion takes place after 30 minutes.

What I claim is:

1. A process for the preparation of 6-demethyl-6-deoxy-6-methylene-tetracycline having the general formula II

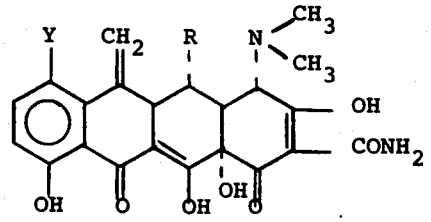

where
Y = H, halogen
R = H —OH —O—COR'
R' = alkyl group containing from 1 to 6 C atoms,
by means of the reductive dehalogenation effected with the employment of tertiary phosphines, arsines or stibines, of 11a-halo-6-demethyl-6-deoxy-6-methylene tetracycline having the general formula I

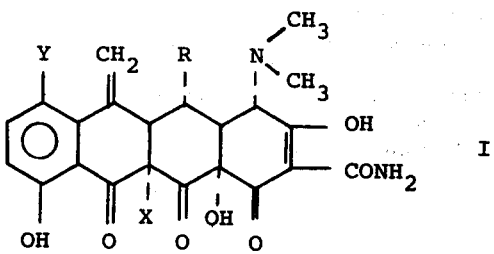

where
Y = H, halogen
R = H, OH, —O—CO—R'
R' = alkyl group containing from 1 to 6 C atoms,
in polar solvents selected from the group consisting of alcohols containing at least one hydroxy group and from 1 to 4 carbon atoms, methoxyethanol, ethoxyethanol, their mixtures and said alcohols or their mixtures with dioxane, tetrahydrofurane, acetonitrile, N,N'-dimethylformamide and acetone, at temperatures comprised between 10°C and 90°C, for periods of time of from 5 minutes to 80 minutes.

2. A process according to claim 1, characterized by the fact that the reagent is triphenylphosphine.

3. The process according to claim 1, wherein said temperature is between 50°C. and 70°C.

4. The process according to claim 1, wherein said period of time is between 20 and 60 minutes.

* * * * *